United States Patent [19]

Pannek, Jr.

[11] Patent Number: 5,192,291

[45] Date of Patent: Mar. 9, 1993

[54] ROTATIONALLY EXPANDABLE ATHERECTOMY CUTTER ASSEMBLY

[75] Inventor: Edward J. Pannek, Jr., Oceanside, Calif.

[73] Assignee: InterVentional Technologies, Inc., San Diego, Calif.

[21] Appl. No.: 820,754

[22] Filed: Jan. 13, 1992

[51] Int. Cl.⁵ .................................................. A61B 17/32
[52] U.S. Cl. ..................................... 606/159; 606/170; 606/180; 604/22
[58] Field of Search ................ 606/159, 170, 127, 128, 606/180, 191, 198; 604/22, 104–108; 128/751–754; 15/104.19

[56] References Cited

U.S. PATENT DOCUMENTS

| | | | |
|---|---|---|---|
| 2,556,783 | 6/1951 | Wallace | 128/321 |
| 2,729,210 | 1/1956 | Spencer | 128/2 |
| 2,730,101 | 1/1956 | Hoffman | 128/305 |
| 2,749,909 | 6/1956 | Ullery et al. | 128/2 |
| 3,320,957 | 5/1967 | Sokolik | 128/311 |
| 3,512,519 | 10/1967 | Hall | 128/2 |
| 3,605,721 | 9/1971 | Hallac | 128/2 B |
| 3,815,604 | 6/1974 | O'Malley et al. | 128/305 |
| 3,990,453 | 11/1976 | Doaves et al. | 128/305 |
| 4,111,207 | 8/1978 | Seiler, Jr. | 128/305 |
| 4,273,128 | 6/1981 | Lary | 128/305 |
| 4,320,762 | 3/1982 | Bentov | 128/343 |
| 4,441,509 | 4/1984 | Kotsifas et al. | 128/757 |
| 4,445,509 | 5/1984 | Auth | 128/305 |
| 4,589,412 | 5/1986 | Kensey | 128/305 |
| 4,598,710 | 7/1986 | Kleinberg | 128/318 |
| 4,603,694 | 8/1986 | Wheeler | 128/312 |
| 4,610,662 | 9/1986 | Weikl et al. | 604/53 |
| 4,627,436 | 12/1986 | Leckrone | 128/303.1 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,650,466 | 3/1987 | Luther | 604/95 |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,706,671 | 11/1987 | Weinrib | 128/348.1 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell | 128/305 |
| 4,857,045 | 8/1989 | Rydell | 604/22 |
| 4,887,613 | 12/1989 | Farr et al. | 606/159 |
| 4,895,166 | 1/1990 | Farr et al. | 128/751 |
| 4,950,277 | 8/1990 | Farr | 606/159 |
| 4,966,604 | 10/1990 | Reiss | 606/159 |
| 4,986,807 | 1/1991 | Farr | 604/22 |
| 5,019,088 | 5/1991 | Farr | 606/159 |
| 5,071,424 | 12/1991 | Reger | 606/159 |

*Primary Examiner*—John D. Yasko
*Assistant Examiner*—William W. Lewis
*Attorney, Agent, or Firm*—Nydegger & Associates

[57] ABSTRACT

A rotationally expandable atherectomy cutter assembly for cutting plaque from a stenosis in an artery includes a plurality of radially separated and axially aligned blade elements. The distal ends of each blade element are fixably connected to a hub and the proximal ends of each blade element slidably engage helical slots formed in a distally flared extension tube of the assembly. The extension tube is connectable to a rotatable catheter. The helical slots are oriented in a first direction such that contact of the cutter assembly with the plaque of the stenosis, in conjunction with a second direction rotation of the catheter causes the proximal ends of the blade assembly to slide distally along the helical slots thereby expanding the cutting radius of the cutter assembly.

17 Claims, 2 Drawing Sheets

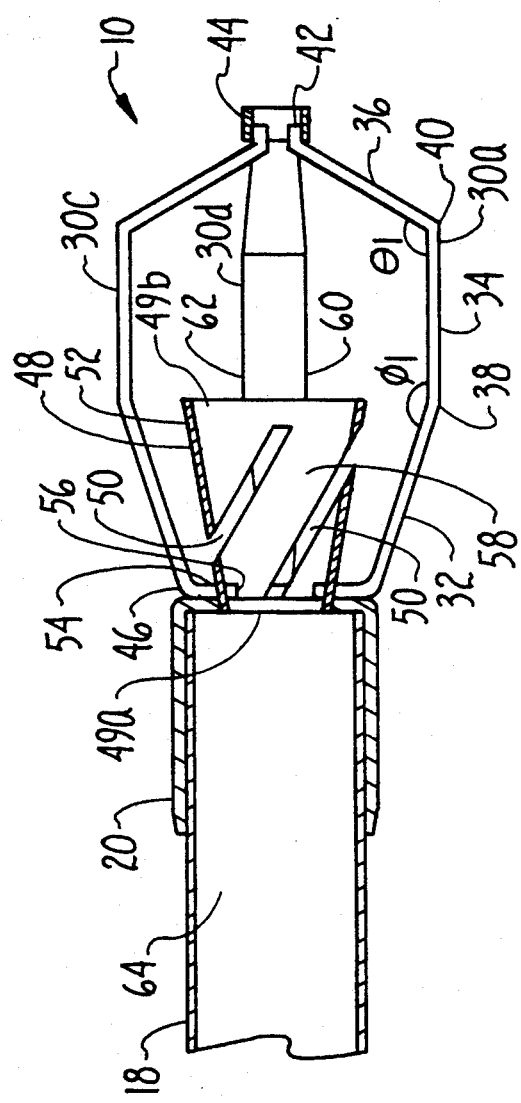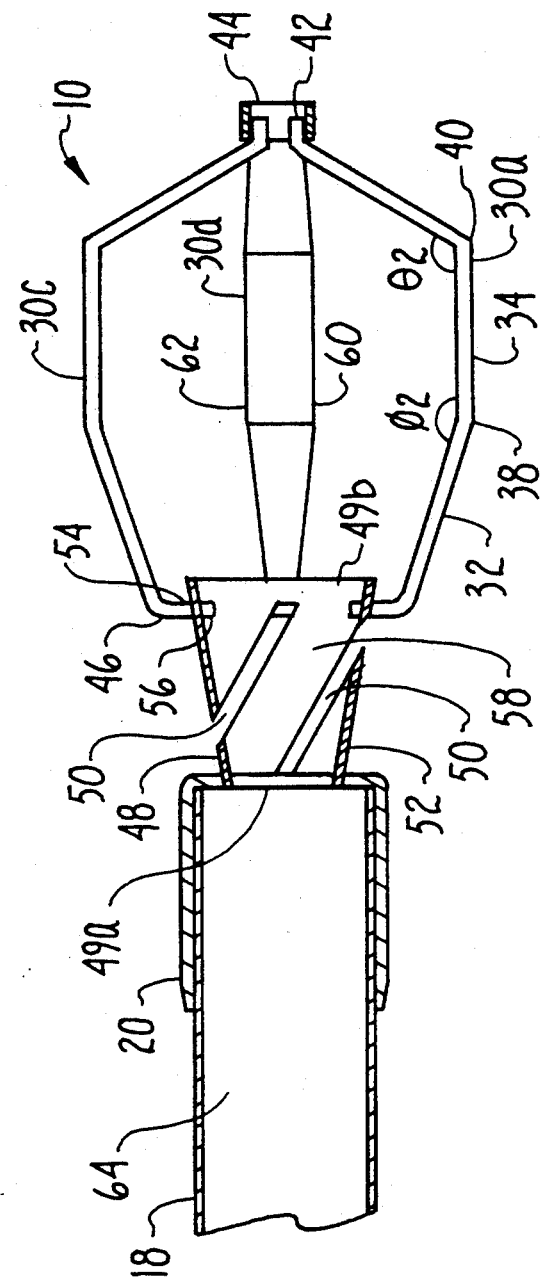

ROTATIONALLY EXPANDABLE ATHERECTOMY CUTTER ASSEMBLY

FIELD OF THE INVENTION

The present invention relates generally to devices which remove stenoses from blood vessels. More particularly, the present invention relates to atherectomy devices. The present invention particularly, though not exclusively, relates to cutter assemblies for atherectomy devices which cut a bore through atherosclerotic plaque.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of arterial blockages reducing arterial blood flow. Consequently, several methods have been introduced to alleviate the effects of plaque build-up restricting the arterial lumen. One such method is a procedure termed angioplasty, which uses an inflatable device positioned in the artery to dilate the lumen at the stenosis. A typical angioplasty device is disclosed in U.S. Pat. No. 4,896,669 to Bhate et al. The angioplasty device of Bhate et al includes an inflatable balloon which is attached to the distal end of a hollow catheter. The proximal end of the catheter is attached to a fluid source, providing fluid communication between the balloon and the fluid source.

To treat an arterial stenosis, the Bhate et al balloon is introduced into the artery in a deflated state and guided through the artery over a guide wire to a position adjacent the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices such as the Bhate et al device do not remove the plaque from the artery. Consequently, the residual plaque either remains in place at the point of the stenosis or breaks off and migrates to other locations in the blood stream. In either case the plaque remains a continuing threat to create blockages in the circulatory system. To address the shortcomings of angioplasty, a procedure termed atherectomy has been devised which cuts and removes the plaque comprising the stenosis from the blood vessel.

An atherectomy procedure typically includes inserting a guide wire into the affected artery and advancing a hollow cutting device over the wire until the cutting device is positioned adjacent the stenosis. The cutting device is then advanced into the stenosis to cut a channel through the plaque, thereby increasing blood flow through the artery. The resulting plaque fragments are removed from the blood stream by drawing them into the hollow cutting device.

A number of atherectomy devices capable of performing this procedure are known in the art. U.S. Pat. No. 4,895,166 to Farr et al, which is assigned to the same assignee as the present invention, discloses an atherectomy device having a frustum-shaped cutter which is attached to the distal end of a hollow catheter. The cutter has two openings that define two straight, even cutting blades. The cutter is directed through the artery over a guide wire, and it is rotated as it advances into the stenosis, thereby cutting the plaque. Excised plaque enters the openings of the cutter and is subsequently removed through the hollow catheter.

While the Farr et al device is effective for its intended purpose, due to the configuration of the cutter blades, a helically-shaped uncut ridge of plaque is occasionally left on the arterial wall as the rotating cutter advances through the stenosis. This ridge of plaque, along with fibers of plaque which extend from the ridge, can act as a site for future blood clotting and ultimately lead to a restenosis of the affected artery. Accordingly, the present invention recognizes a need to provide an atherectomy device which cuts a channel through a stenosis, wherein the channel extends radially out to the arterial wall and has a smooth bore substantially free of plaque.

It is therefore an object of the present invention to provide an atherectomy cutter assembly that can cut a channel through a stenosis in a blood vessel of a living being. Another object of the present invention is to provide an atherectomy cutter assembly that cuts a channel through an arterial stenosis wherein the channel can be radially expanded to the arterial wall. Finally, it is an object of the present invention to provide an atherectomy cutter assembly which is relatively easy to use and cost-effective to manufacture.

SUMMARY OF THE INVENTION

The atherectomy device of the present invention is a cutter assembly which is attachable to the distal end of a rotatable catheter. The cutter assembly has a plurality of blade elements which are double-edged bands radially disposed about the longitudinal axis of the cutter assembly. Each blade element has a proximal section, an intermediate section, and a distal section. The intermediate section includes a cutting edge and is aligned substantially parallel to the longitudinal axis of the cutter assembly. The proximal and distal sections of each blade element extend from the intermediate section toward the longitudinal axis of the assembly.

The distal ends of the blade elements are all fixably attached to a hub at the longitudinal axis of the cutter assembly, while the proximal ends of the blades are slidably attached to a distally flared extension tube that extends coaxially with the longitudinal axis of the cutter assembly. Slidable attachment is provided by a plurality of helical slots formed in the wall of the extension tube. Each slot is associated with a single blade element, and more particularly the proximal end of each blade element engages a slot such that the proximal end of the element is free to slide along the length of the helical slot.

Attachment of the cutter assembly to the hollow catheter is provided by connecting the extension tube to the distal end of the catheter. The connection is enabled by a union into which both the extension tube and catheter fit at opposite ends thereof. Consequently, rotation of the catheter translates into rotation of the blade elements. The cutting edge, i.e., cutting blade, of each blade element is the leading edge (relative to the direction of rotation) of the intermediate section.

The cutter assembly is capable of assuming various diameters which are functionally related to the location of the blade elements' proximal ends along the length of the helical slots. When the cutter assembly is in a contracted position which corresponds to its smallest diameter, the proximal ends of the blade elements are positioned at the proximal ends of each slot. If it is desire to increase the diameter of the cutter assembly, the proximal ends of the blade elements are slid distally in the slots, thereby radially displacing the proximal section of each blade element away from the longitudinal axis of the cutter assembly in correspondence with the degree of flaring at the distal end of the extension tube.

The net effect of distally sliding the proximal end of the blade element in the slot is to elastically bend the blade element at the intersection of the proximal and intermediate sections as well as at the intersection of the distal and intermediate sections. Bending of these intersections urges the intermediate section away from the longitudinal axis of the cutter assembly, while maintaining the section in substantially parallel orientation with the axis. Consequently, the cutter assembly assumes an expanded position of increased diameter.

The above-described expansion procedure is performed within the body during operation of the cutter assembly in accordance with the present invention. In particular, the cutter assembly is operated by positioning it on the distal end of the catheter while maintaining the assembly in a contracted position. The assembly is inserted into an artery to be treated and guided through the artery to the stenosis, typically along a guide wire previously inserted into the artery. The cutter assembly is urged into the stenosis such that the cutting blades abut the plaque while rotating the catheter and assembly in a direction substantially opposite the rotational orientation of the helical slots in the expansion tube. When the blade elements are pushed against the plaque, the cutter assembly encounters a resistance to rotation which causes the proximal ends of the blade elements to slide distally in the slots. Consequently the blade elements are expanded and the diameter of the cutting assembly is increased.

The expanded assembly is driven through the entire stenosis, cutting a channel therethrough which preferably extends to the artery wall. The cuttings can be collected in the distal end of the hollow catheter as the cutter assembly advances through the stenosis. Upon completion of the channel through the stenosis, the assembly is withdrawn back out through the artery. The cutter assembly resumes the contracted position during withdrawal and damage to the artery wall is accordingly minimized.

The novel features of this invention, as well as the invention itself, both as to its structure and its operation, will be best understood from the accompanying drawing, taken in conjunction with the accompanying description, in which similar reference characters refer to similar parts.

BRIEF DESCRIPTION OF THE DRAWINGS

FIG. 3 is a cross-sectional view of the atherectomy cutter assembly of the present invention in a contracted position.

FIG. 4 is a cross-sectional view of the atherectomy cutter assembly of the present invention in an expanded position.

DESCRIPTION OF THE PREFERRED EMBODIMENT

Figure 1:
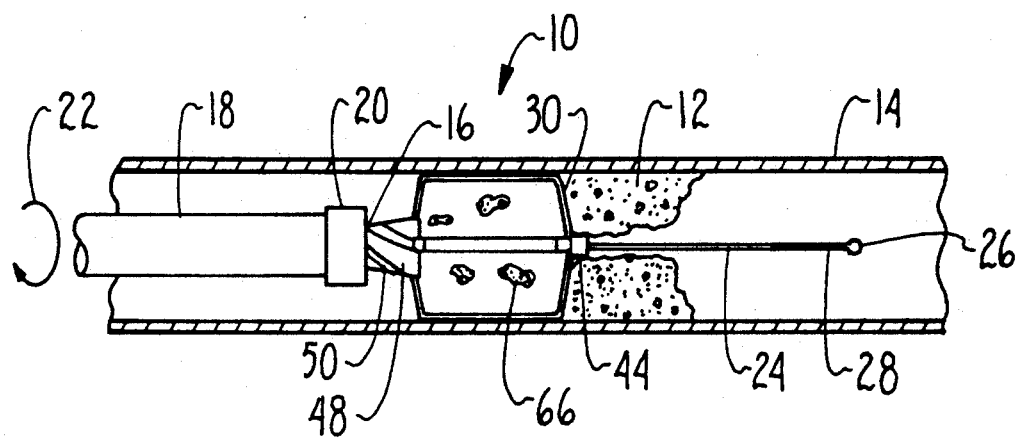
FIG. 1 is a schematic view of the atherectomy cutter assembly of the present invention in its intended environment.

Referring initially to FIG. 1, an atherectomy cutter assembly generally designated 10 is shown cutting a substantially smooth bore through a stenosis 12 which is formed on the interior wall of an artery 14. As shown, cutter assembly 10 is attached at its proximal end 16 to a hollow rotatable catheter 18. Cutter assembly 10 is coaxially attached to hollow catheter 18 by means of a union 20. Catheter 18 is any suitable tubular structure which can transmit torque, e.g., in the direction indicated by clockwise arrow 22, from a motor (not shown) to cutter assembly 10.

FIG. 1 shows that the cutter assembly 10 can be steered to the stenosis 12 within artery 14 over a flexible guide wire 24. As shown, guide wire 24 extends through torque tube 18 and atherectomy cutter assembly 10. Guide wire 24 can include a stop 26 which is formed on the distal end 28 of guide wire 24. The diameter of stop 26 is larger than the diameter of distal end 28 to prevent the withdrawal of guide wire 24 from atherectomy cutter assembly 10.

The materials of atherectomy cutter assembly 10 are preferably lightweight and strong, as well as chemically inert with the body tissue of artery 14. For example, atherectomy cutter assembly 10 can be made of 400 series stainless steel. Similarly, guide wire 24 can be a flexible yet strong stainless steel wire.

Figure 2:
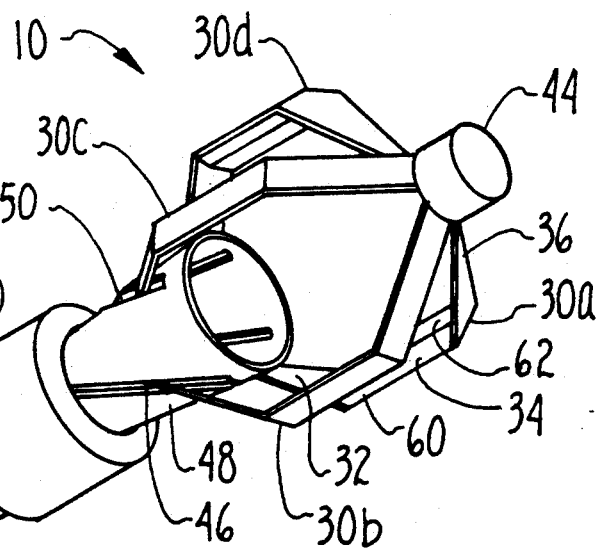
FIG. 2 is a perspective view of the atherectomy cutter assembly of the present invention.

The details of atherectomy cutter assembly 10 are best seen in cross-reference to FIGS. 2, 3, and 4. FIG. 2 shows that cutter assembly 10 includes a plurality of blade elements 30a, 30b, 30c, 30d, which are radially disposed about the longitudinal axis of cutter assembly 10 and each of which are substantially identically configured.

Representative blade element 30a has the configuration of a double-edged band which is segmented into three distinct sections, i.e., a proximal section 32, an intermediate section 34, and a distal section 36. Intermediate section 34 is aligned substantially parallel to the longitudinal axis of cutter assembly 10. Proximal section 32 extends from one end of intermediate section 34 toward the longitudinal axis of cutter assembly 10, and similarly distal section 36 extends from the opposite end of intermediate section 34 toward the longitudinal axis.

The intersection 38 between the intermediate and proximal sections of blade element 30a defines an obtuse angle $\phi$ and the intersection 40 between the intermediate and distal sections defines an obtuse angle $\beta$. Although the respective sections of blade elements 30a are relatively rigid, intersections 38 and 40 are somewhat flexible and accordingly act as hinges about which blade sections 32 and 36 can pivot in a manner described hereafter.

The distal ends 42 of blade elements 30a, 30b, 30c, 30d intersect to form a hub 44 on the longitudinal axis of cutter assembly 10. Blade elements 30a, 30b, 30c, 30d are fixably attached to one another at hub 44 by a fastening means such as a grommet shown in FIGS. 1–4. The proximal ends 46 of blade elements 30a, 30b, 30c, 30d are slidably attached to an extension tube 48 that is positioned coaxially with the longitudinal axis of cutter assembly 10. Extension tube 48 is distally flared such that the proximal opening 49a is narrower than the distal opening 49b. Slidable attachment between proximal ends 46 and extension tube 48 is provided by a plurality of helical slots 50 formed in the wall 52 of extension tube 48. Each proximal end 46 engages a slot 50 and is free to slide along the length of slot 50.

Proximal end 46 has a portion 54 near its tip which is narrower than slot 50 and fits therein. Proximal end 46, however, is restricted from disengaging slot 50 by tab 56 positioned beyond narrow portion 54 at the tip of proximal end 46. Tab 56 resides in the open interior 58 of extension tube 48 and has a width greater than the width of slot 50.

Intermediate section 34 of blade element 30 has opposite edges 60 and 62. Edge 60 is the sharpened leading edge as defined by the clockwise direction of rotational arrow 22. Edge 60 is termed a radial cutting blade and is a relatively straight and even blade that is free of teeth. Edge 62 is the unsharpened following edge. It is understood that cutting assembly 10 can be rotated in a counter-clockwise direction opposite that indicated by arrow 22, in which case edge 62 is sharpened and becomes the radial cutting blade, while edge 60 becomes the following edge. It is further understood that the corresponding edges of distal section 36 can be sharpened in the same manner as edges 60 and 62 to provide relatively straight and even frontal cutting blade in addition to, or in substitution of, the above-described radial cutting blade.

Catheter 18, union 20 and extension tube 48 are all hollow and substantially cylindrical in shape. Catheter 18 and extension tube 48 are coaxially aligned within union 20 in an interference fit therewith. If desired, catheter 18 and extension tube 48 can be epoxy-bonded or spot welded to union 20. Alternatively, union 20 can be formed integrally with sleeve extension tube 48, e.g. by forging or casting union 20 with extension tube 48 in accordance with common metallurgical principles.

In any case, union 20 and extension tube 48 provide a continuous passage 64 of fluid communication from blade elements 30 into catheter 18. Thus, cuttings 66 from stenosis 12, as shown in FIG. 1, may be deposited into catheter 18 for subsequent withdrawal from the artery. Deposition of the cuttings 66 into catheter 18 may be facilitated by providing a suction means (not shown) at the proximal end of catheter 18 in a manner known to one skilled in the art.

A characteristic of cutter assembly 10 is that its diameter automatically adjusts in situ. With reference to FIG. 3, cutter assembly 10 is shown in a fully contracted position which corresponds to the smallest diameter of adjustment. Proximal ends 46 of blade elements 30 are positioned proximally within slots 50 adjacent union 20 and proximal opening 49a of extension tube 48. FIG. 4 shows cutter assembly 10 in a fully expanded position which corresponds to the greatest diameter of adjustment. Proximal ends 46 are positioned distally within slots 50 adjacent distal opening 49b of extension tube 48. It is noted that angles $\phi_1$ and $\beta_1$ of intersections 38 and 40 respectively in FIG. 3 are somewhat greater than angles $\phi_2$ and $\beta_2$ of corresponding intersections in FIG. 4 due to the flexing of intersections 38 and 40 when assembly 10 transitions between the contracted and expanded positions as described hereafter.

Adjustment of cutter assembly 10 between the contracted and expanded positions is accomplished by applying a resistance force against the rotation of blade elements 30, wherein the rotation has a direction of curvature corresponding to clockwise arrow 22. Since slots 50 are oriented in a substantially counter-clockwise direction of downward curvature opposite that of arrow 22, the resistance force causes proximal ends 46 of blade elements 30 to slide distally within slots 50 which in turn displaces proximal sections 32 radially away from the longitudinal axis of cutter assembly 10 in correspondence with the flaring of extension tube 48. Displacement of proximal sections 32 bends intersections 38 and 40 to diminish angles $\phi$ and $\beta$, thereby urging cutting blades 60 away from the longitudinal axis of cutter assembly 10 and increasing the cutting radius thereof.

OPERATION

In the operation of atherectomy cutter assembly 10, reference is initially made to FIG. 1. In accordance with well-known surgical techniques, guide wire 24 is positioned within artery 14 and catheter 18 having atherectomy cutter assembly 10 attached thereto is advanced over wire 24 until assembly 10 is positioned adjacent stenosis 12. Throughout placement of cutter assembly 10, it is maintained in its contracted position.

Once assembly 10 is adjacent stenosis 12, catheter 18 is rotated, which also causes cutter assembly 10 to rotate. As cutter assembly 10 rotates, it is advanced into stenosis 12 where plaque is encountered Which Causes a resistance to rotation. Accordingly, cutter assembly 10 expands while progressing forward to out a wide and substantially smooth channel therethrough. Plaque cuttings 66 which are excised by blade 60 are drawn into passage 64 by applying a vacuum thereto.

Upon completion of the channel through stenosis 12, assembly 10 is withdrawn back out through artery 14 along with cuttings 66. Cutter assembly 10 resumes the contracted position during withdrawal and damage to the artery wall is accordingly minimized.

While the particular atherectomy cutter assembly as herein shown and disclosed in detail is capable of obtaining the objects and providing the advantages hereinbefore stated, it is understood that this particular assembly is merely illustrative of presently preferred embodiments of the invention. It is further understood that the present invention is not intended to be so limited and that other embodiments are further possible within the scope of the present invention.

I claim:

1. An atherectomy cutter assembly having a longitudinal axis, said cutter assembly comprising:
   a plurality of blade elements radially spaced about said longitudinal axis, each of said blade elements having a distal end and a proximal end;
   a hub at said distal ends of said blade elements wherein said distal ends of said blade elements are fixably connected to said hub; and
   an extension tube positioned coaxially with said blade elements, said tube having a plurality of helical slots formed therein extending in a direction of said longitudinal axis and slidably retaining each of said proximal ends of said blade elements.

2. An atherectomy cutter assembly as recited in claim 1 wherein said extension tube is distally flared.

3. An atherectomy cutter assembly as recited in claim 1 wherein said extension tube is substantially cylindrical and hollow with openings at a proximal end and a distal end of said tube.

4. An atherectomy cutter assembly as recited in claim 1 further comprising a tubular union engaging said extension tube and connectable to a hollow catheter.

5. An atherectomy cutter assembly as recited in claim 4 wherein said union and said extension tube form a continuous passageway from said blade elements to said hollow catheter.

6. An atherectomy cutter assembly as recited in claim 4 wherein said union is integral with said extension tube.

7. An atherectomy cutter assembly having a longitudinal axis, said cutter assembly comprising:
- a plurality of blade elements radially spaced about said longitudinal axis, each of said blade elements having a distal end, a proximal end, and a cutting blade oriented substantially parallel to said longitudinal axis;
- a hub at said distal ends of said blade elements wherein said distal ends of said blade elements are fixably connected to said hub; and
- an extension tube positioned coaxially with said blade elements, said tube having a plurality of slots formed therein extending in a direction of said longitudinal axis and slidably retaining each of said proximal ends of said blade elements.

8. An atherectomy cutter assembly as recited in claim 7 wherein said cutting blades define a cutting radius greater than the radius of said extension tube.

9. A rotationally expandable atherectomy cutter assembly having a longitudinal axis, said cutter assembly comprising:
- a plurality of blade elements radially spaced about said longitudinal axis, each of said blade elements having a distal end, a proximal end and a cutting blade therebetween oriented substantially parallel to said longitudinal axis;
- a hub at said distal ends of said blade elements wherein said distal ends of said blade elements are fixably connected to said hub;
- a distally flared extension tube positioned coaxially with said blade elements, wherein said tube is substantially cylindrical and hollow and has openings at a proximal end and a distal end of said tube;
- a union engaging said extension tube and connectable to a hollow catheter to form a continuous passageway from said blade elements to said hollow catheter; and
- a plurality of helical slots formed in said tube wherein each of said proximal ends of said blade elements is slidably retained in one of said slots, and wherein said tube is rotatable about said axis in a first direction of curvature and said plurality of helical slots are oriented in a second direction of curvature substantially opposite said first direction of curvature such that when said cutter assembly encounters resistance to rotation in said first direction of curvature, said proximal ends of said blade elements slide distally along said slots, thereby expanding the cutting radius of said cutting blades.

10. A rotationally expandable atherectomy cutter assembly as recited in claim 9 wherein said cutting blades define a cutting radius greater than the radius of said extension tube.

11. A rotationally expandable atherectomy cutter assembly as recited in claim 9 wherein said union is integral with said extension tube.

12. An atherectomy cutter assembly having a longitudinal axis and rotationally expandable from a contracted position to an expanded position, said cutter assembly comprising:
- a plurality of blade elements radially spaced about said longitudinal axis, each of said blade elements having a distal end, a proximal end and a cutting blade therebetween oriented substantially parallel to said longitudinal axis;
- a hub at said distal ends of said blade elements wherein said distal ends of said blade elements are fixably connected to said hub;
- a distally flared extension tube positioned coaxially with said blade elements;
- a plurality of helical slots, each having a proximal and distal end, formed in said tube, wherein each of said proximal ends of said blade elements is slidably retained in one of said slots, and wherein said tube is rotatable about said axis in a first direction of curvature and said plurality of helical slots are oriented in a second direction of curvature substantially opposite said first direction of curvature;
- further wherein said proximal ends of said blade elements substantially abut said proximal ends of said slots when said assembly is in said contracted position and said proximal ends of said blade elements substantially abut said distal ends of said slots when said assembly is in said expanded position, and wherein transition from said contracted position to said expanded position is actuated when said cutter assembly encounters resistance to rotation in said first direction of curvature.

13. An atherectomy cutter assembly as recited in claim 12 wherein said cutting blades define a cutting radius greater than the radius of said extension tube.

14. An atherectomy cutter assembly as recited in claim 13 wherein the cutting radius of said cutting blades is greater in said expanded position than in said contracted position.

15. An atherectomy cutter assembly as recited in claim 12 wherein said extension tube is substantially cylindrical and hollow with openings at a proximal end and a distal end of said tube.

16. An atherectomy cutter assembly as recited in claim 12 further comprising a tubular union engaging said extension tube and connectable to a hollow catheter.

17. An atherectomy cutter assembly as recited in claim 16 wherein said union and said extension tube form a continuous passageway from said blade elements to said hollow catheter.

* * * * *